(12) United States Patent
Fischer

(10) Patent No.: US 6,422,865 B1
(45) Date of Patent: Jul. 23, 2002

(54) ENDODONTIC IRRIGATOR TIPS HAVING CANNULAS WITH ANNEALED DISTAL PORTIONS AND RELATED METHODS

(75) Inventor: Dan E. Fischer, Sandy, UT (US)

(73) Assignee: Ultradent Products, Inc., South Jordan, UT (US)

(*) Notice: Subject to any disclaimer, the term of this patent is extended or adjusted under 35 U.S.C. 154(b) by 0 days.

(21) Appl. No.: 09/766,721

(22) Filed: Jan. 22, 2001

(51) Int. Cl.$^7$ ................................................ A61C 17/00
(52) U.S. Cl. ............................................. 433/81; 604/264
(58) Field of Search ........................... 433/80, 81, 224; 604/264, 272, 523

(56) References Cited

U.S. PATENT DOCUMENTS

| | | |
|---|---|---|
| 2,482,622 A | 9/1949 | Kahn |
| 3,624,907 A | 12/1971 | Brass et al. |
| 3,816,921 A | 6/1974 | Malmin |
| 4,011,869 A | 3/1977 | Seiler, Jr. |
| 4,813,928 A | 3/1989 | Abe et al. ............... 604/49 |
| 4,921,775 A | 5/1990 | Buchanan ............... 433/102 |
| 4,993,941 A | 2/1991 | Maita et al. ............ 433/80 |
| 5,092,854 A * | 3/1992 | Black ..................... 604/243 |
| 5,114,402 A | 5/1992 | McCoy .................... 604/95 |
| 5,127,831 A | 7/1992 | Bab ........................ 433/80 |
| 5,231,989 A | 8/1993 | Middleman et al. |
| 5,345,937 A | 9/1994 | Middleman et al. |
| 5,378,149 A | 1/1995 | Stropko ................... 433/80 |
| 5,626,473 A * | 5/1997 | Muhlbauer et al. ..... 433/89 |
| 5,752,825 A | 5/1998 | Buchanan ............... 433/32 |
| 5,836,764 A | 11/1998 | Buchanan ............... 433/102 |
| 5,842,861 A | 12/1998 | Buchanan ............... 433/102 |
| 5,897,316 A | 4/1999 | Buchanan ............... 433/102 |
| 6,079,979 A * | 6/2000 | Riitano ................... 433/81 |
| 6,168,432 B1 * | 1/2001 | Marlin .................... 433/81 |

* cited by examiner

Primary Examiner—Ralph A. Lewis
(74) Attorney, Agent, or Firm—Workman, Nydegger, Seeley

(57) ABSTRACT

An endodontic irrigator tip having a cannula with an annealed distal portion and a proximal portion enables the cannula to easily move within a root canal. The cannula extends from a hub that is adapted for coupling with a syringe or other delivery device. The cannula has an outlet orifice for delivering an irrigant out of the endodontic irrigator tip and into the root canal. The outlet orifice may be defined by a rounded rim that optimally enables the distal insertion end of the cannula to be advanced within the root canal.

23 Claims, 7 Drawing Sheets

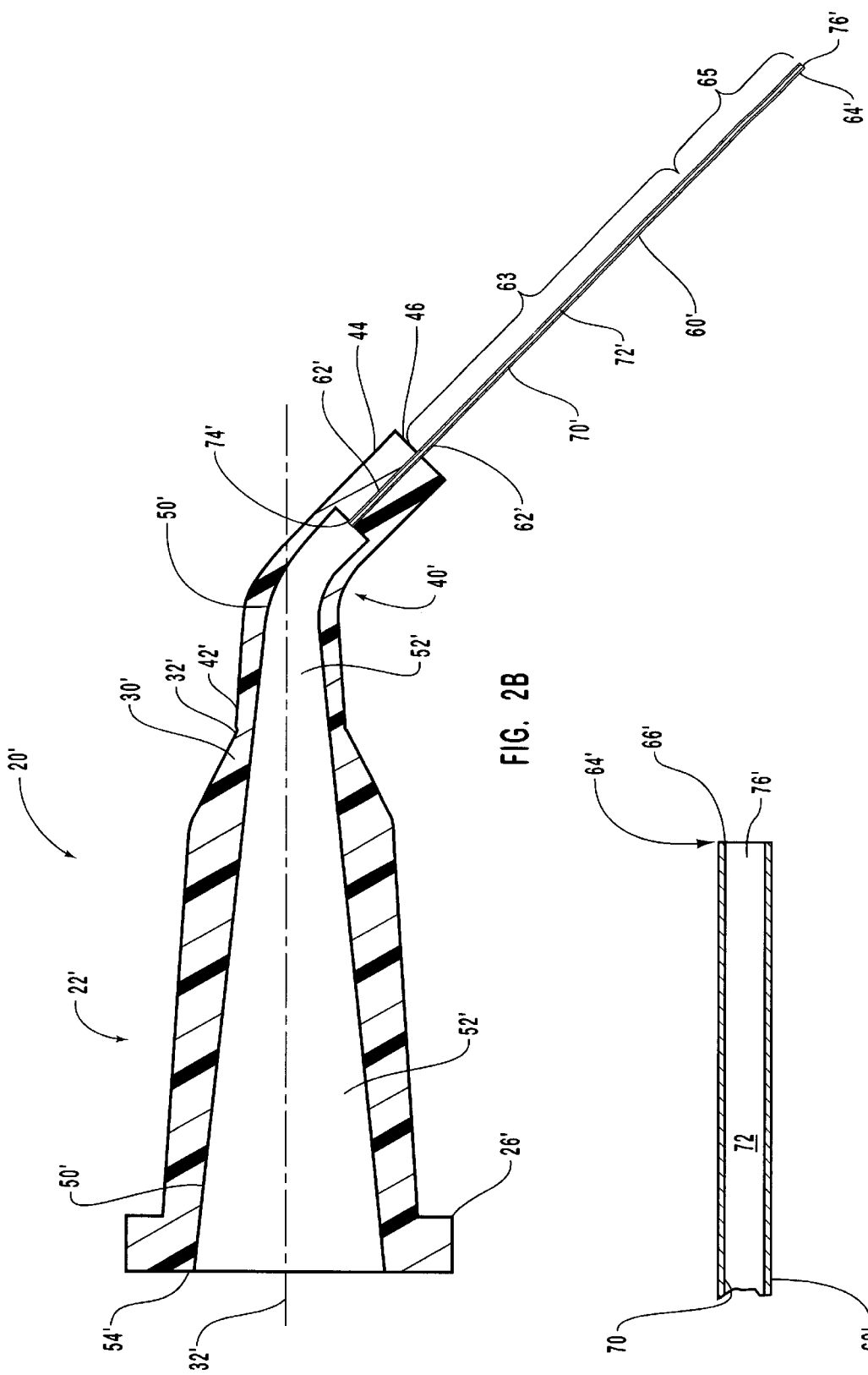

ENDODONTIC IRRIGATOR TIPS HAVING CANNULAS WITH ANNEALED DISTAL PORTIONS AND RELATED METHODS

BACKGROUND OF THE INVENTION

1. The Field of the Invention

This invention is in the field of instruments for use in medicine and dentistry. More specifically, this invention is in the field of endodontic irrigator tips for irrigating root canals as part of a root canal procedure.

2. The Relevant Technology

To preserve a tooth that has a diseased pulp cavity, it is necessary to prevent bacterial proliferation within the pulp canal of the tooth by removing the diseased or necrotic pulp material from the pulp canal. After the pulp material has been removed or extirpated from a tooth, the pulp cavity is typically filled or obturated with a material such as gutta percha to occlude the pulp cavity and a sealer to seal the pulp cavity. This procedure is referred to as root canal therapy. Root canal cleaning is generally achieved by hand or mechanical instrumentation with files that are configured to bore and cut.

It is also common during the root canal procedure to irrigate a pulp cavity and the various root canals involved using an endodontic irrigator tip. Irrigation assists in removing debris and necrotic material cut by the endodontic files and bores. Disinfecting solutions can also be employed in irrigation, thereby disinfecting the pulp cavity and root canals during the operative procedure.

Although, the irrigant preferably is capable of dissolving or disrupting soft tissue remnants to permit their removal, the irrigant may be any suitable liquid such as water or various alcohols. More particularly, although some degree of debridement is preferred, any fluid may be used to flush debris from the root canal. General examples of appropriate irrigants include hydrogen peroxide, primarily for use in the canals of living teeth, or sodium hypochlorite, primarily for the canals in necrotic teeth. A preferred irrigant is the aqueous sodium hypochlorite solution sold as ChlorCid® by Ultradent Products, Inc which contains about 2.5–3% NaOCL. The irrigant may also be a chelator or calcium remover such as EDTA solutions or citric acid solutions. A preferred chelator is sold as File-Eze® by Ultradent Products Inc. which is a 19% EDTA water soluble viscous solution. File-Eze® is a preferred chelator as it is also a lubricant.

One problem associated with the use of conventional endodontic irrigator tips is the potential for the formation of ledges within the root canal. Ledges can occur when a practitioner attempts to insert the distal insertion end of an irrigator tip as far as the apex of the root canal and the distal insertion end is halted prematurely against the sidewall of the root canal. The downward pressure exerted on the distal insertion end causes the end to dig into the side of the root canal and form a ledge. Such ledges are difficult to bypass; and if the ledge occurs very close to the apex, the ledge may give the practitioner the mistaken impression that the apex has been reached. Accordingly, there is a need for irrigator tips that can be used in root canal surfaces with minimal risk of ledging. There is a further need within the art for different irrigator tips which can be used to clean root canal surfaces that are efficient to manufacture.

SUMMARY AND OBJECTS OF THE INVENTION

It is therefore an object of the invention to provide an improved endodontic irrigator tip.

It is another object of the invention to provide an endodontic irrigator tip having a cannula that can be conveniently used to maneuver within the root canal while delivering an irrigant in a manner that minimizes the potential for ledging and that enables the distal insertion end of the cannula to reach as far as is desired within the root canal.

An additional object of the invention to provide irrigation tips that are efficient to manufacture.

The endodontic irrigator tip of the present invention comprises a cannula extending from a hub. The cannula has a distal portion that has been annealed so that it is more flexible than the remainder of the cannula. The annealed distal portion is preferably only a small segment of the cannula. The rigidity and length of the nonannealed portion of the cannula enables the cannula to be responsive to the movements of the hub and to be moved as desired within the root canal. The flexibility of the annealed distal portion enables the distal portion to optimally adjust to the curvatures of the root canal.

The hub has a body with a proximal end adapted for coupling to a syringe. The hub also has a neck having a proximal end coupled to the distal end of the body. The neck has a distal end which may be configured with a flat face to optimally prevent the placement of the irrigator tip past a desired location. A hollow chamber is located in the hub which is defined by an interior surface. The hollow chamber extends through the body and the neck and has an inlet such that fluid can be received from a syringe.

The cannula has a distal insertion end and a proximal end sheathed within the distal end of the neck. Thus, a portion of the cannula extends from the distal end of the neck with sufficient length to extend into a root canal of a tooth. An interior surface of the cannula defines a conduit in fluid communication with the hollow chamber. The cannula has an orifice located at the distal insertion end thereof. The outlet orifice is defined by a rim that is preferably rounded instead of squared. The rounded rim works in conjunction with the annealed portion so that as the annealed portion is flexed, the rim does not dig into surfaces that it contacts and is able to be advanced within the root canal. A cannula that is not annealed along any portion of its length and that has a rounded rim may also be utilized.

These and other objects and features of the present invention will become more fully apparent from the following description and appended claims, or may be learned by the practice of the invention as set forth hereinafter.

BRIEF DESCRIPTION OF THE DRAWINGS

In order that the manner in which the above-recited and other advantages and objects of the invention are obtained, a more particular description of the invention briefly described above will be rendered by reference to a specific embodiment thereof which is illustrated in the appended drawings. Understanding that these drawings depict only a typical embodiment of the invention and are not therefore to be considered to be limiting of its scope, the invention will be described and explained with additional specificity and detail through the use of the accompanying drawings in which:

FIG. 2B is a cross sectional view of the endodontic irrigation tip shown in FIG. 2A.

FIG. 2C is an enlarged cross sectional view of the distal insertion end shown in FIG. 2A.

DETAILED DESCRIPTION OF THE PREFERRED EMBODIMENTS

The present invention relates to an endodontic irrigator tip used with endodontic instruments to deliver materials into a root canal. For example, the tips may be conveniently used to delivery of a variety of different liquids to a root canal, such as debreeding agents, lubricants, anti-bacterial agents, chelating agents, water, hypochlorites, $H_2O_2$, EDTA, sealing or filling materials in combination with syringes or other devices. Most typically, the tips are used with endodontic irrigators and endodontic aspirators.

Figure 1A:
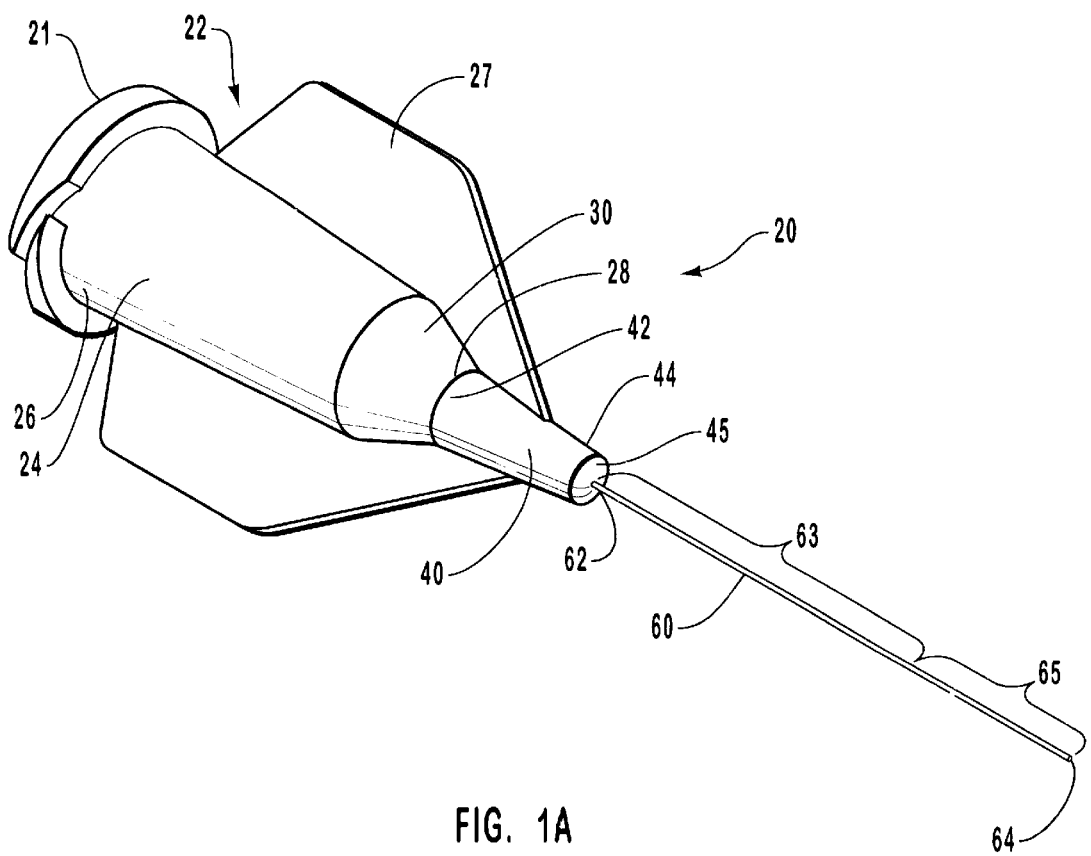
FIG. 1A is a perspective view of a endodontic irrigator tip having a cannula with an annealed distal portion.
Figure 1B:
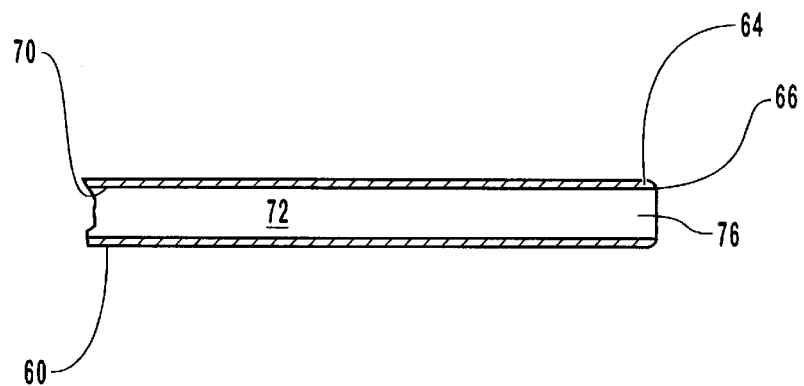
FIG. 1B is an enlarged cross sectional view of the distal insertion end shown in FIG. 1A.

As shown in FIGS. 1A–1B, the primary components of endodontic irrigator tip 20 include a hub 22 having a hollow chamber 52 and a cannula 60 that extends from hub 22 so that it is in fluid communication with the hollow chamber. Cannula 60 has a proximal end 62 adjacent to hub 22 and opposite from the terminus of cannula 60, referred to herein as the distal insertion end 64. A segment of cannula 60 beginning at distal insertion end 64 has been annealed to have greater flexibility than the remainder of cannula 60, this segment is referred to herein as the distal portion 65 or the annealed distal portion. The nonannealed portion of cannula 60 above annealed distal portion 65 is identified at 63. A method for annealing distal portion 65 is described below in detail.

Figure 2A:
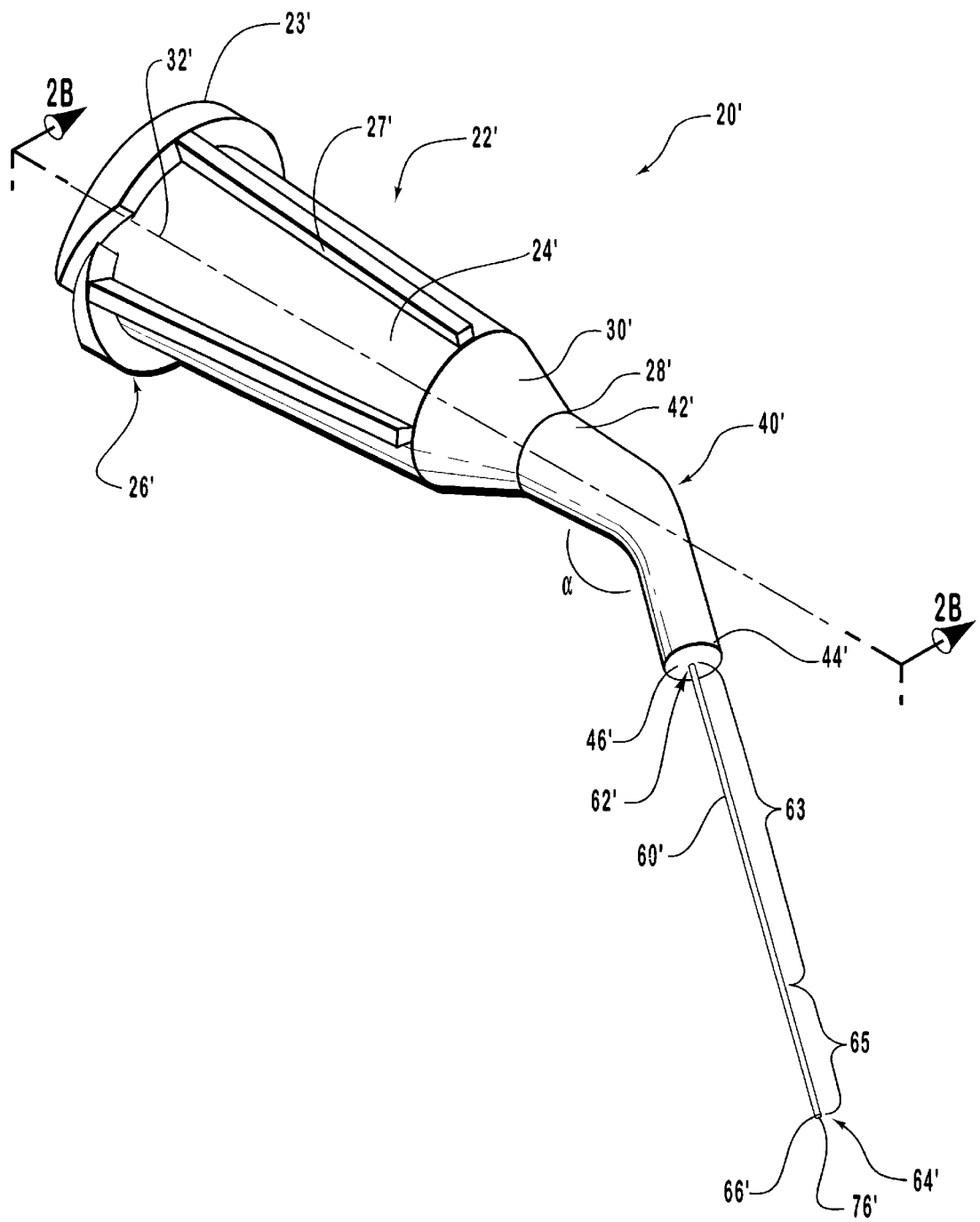
FIG. 2A is a perspective view of another endodontic irrigator tip having a cannula with an annealed distal portion.
Figure 3A:
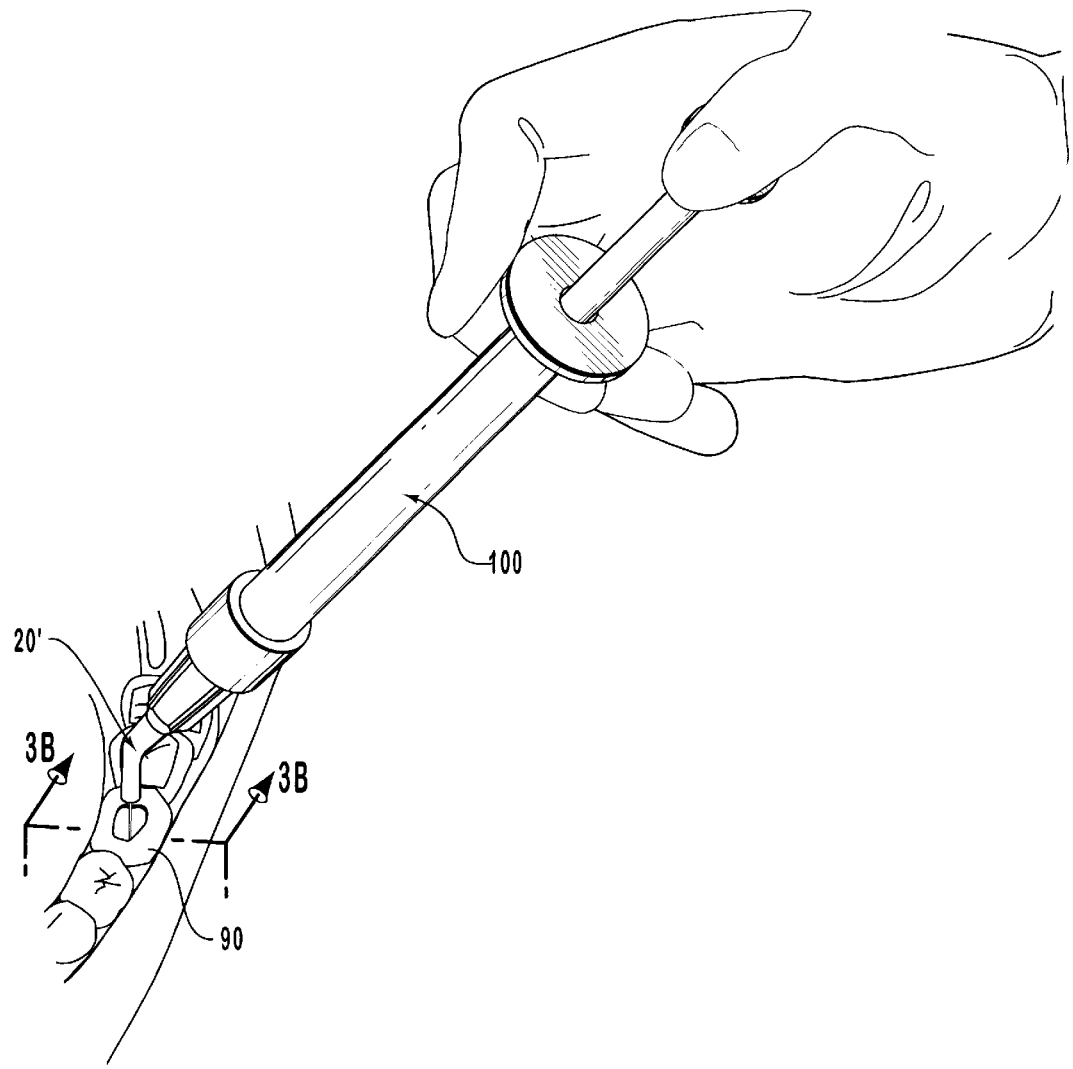
FIG. 3A depicts the endodontic irrigation tip of FIGS. 2A–2C inserted into a tooth.
Figure 3B:
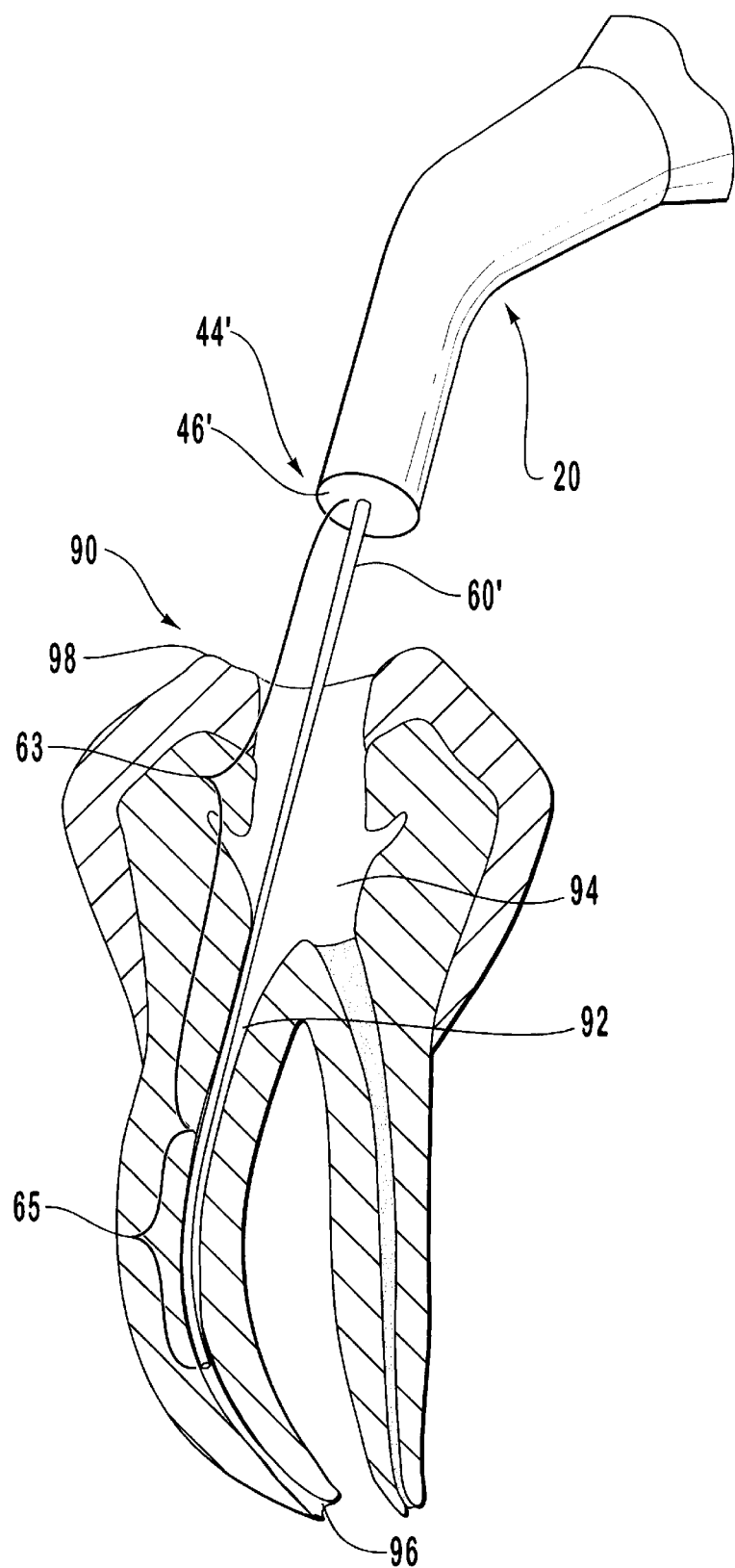
FIG. 3B is a view of a cross section of a tooth with a cannula of the endodontic irrigation tip shown in FIGS. 2A–2C being inserted with its distal portion curving.
Figure 3C:
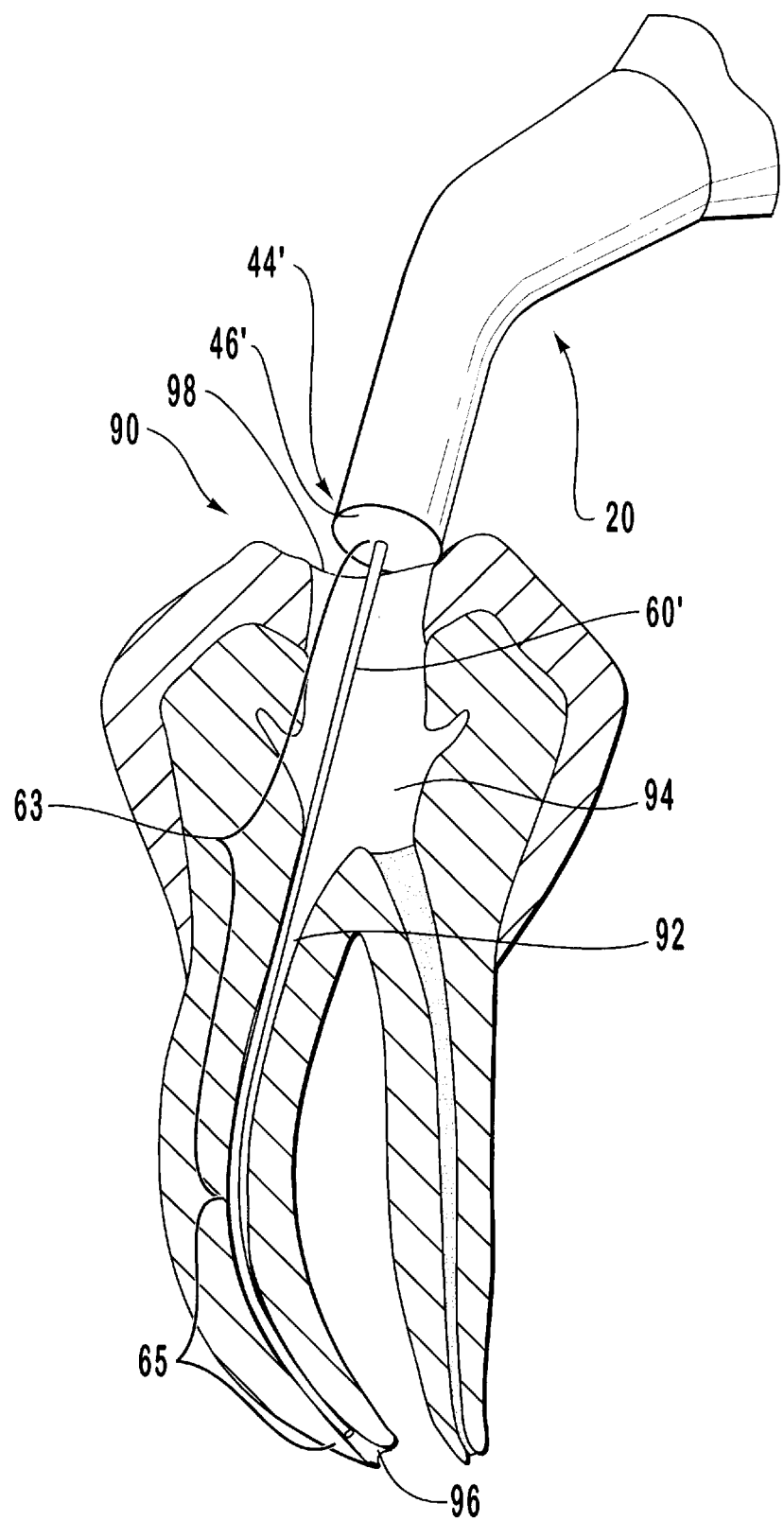
FIG. 3C is a view of a cross section of the tooth shown in FIGS. 3B after the distal portion has been curved in conformance with the curvature of the root canal and approached the apex of the root canal.
Figure 4A:
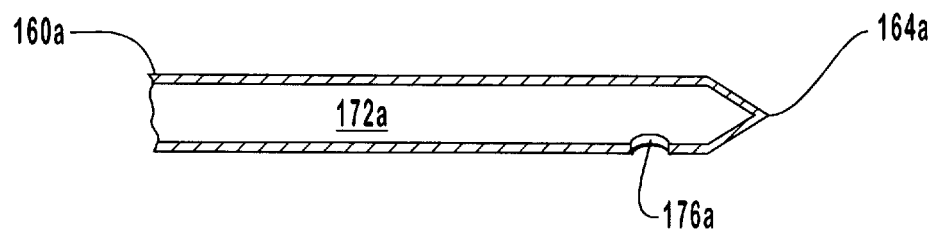
FIG. 4A provide is a cross sectional view of a distal insertion end of an irrigation tip.
Figure 4B:
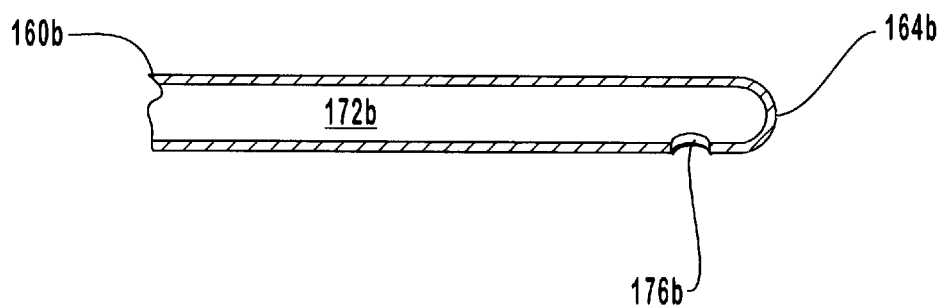
FIG. 4B is a cross sectional view of a distal insertion end of another irrigation tip.
Figure 4C:
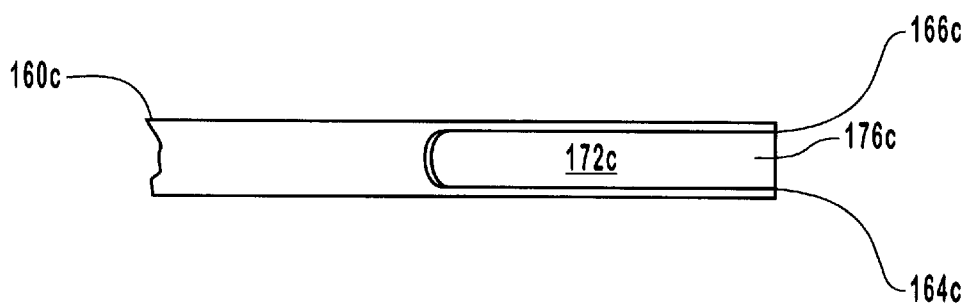
FIG. 4C is a perspective view of a distal insertion end of another irrigation tip.

Another embodiment of the inventive endodontic irrigator tip is shown in FIGS. 2A–2C at 20'. This embodiment is shown being utilized in FIGS. 3A–3C to demonstrate the advantages achieved through the use of an irrigator tip having a cannula with an annealed distal portion. Note that the distal insertion ends of tips 20 and 20' are contrasted respectively in FIG. 1C and FIG. 2B. Other distal insertion ends of cannulas and their respective outlet orifices are shown in FIGS. 4A–4C. Before discussing each of these embodiments in detail, the annealing procedure is first discussed and reference is made to FIGS. 3A–3C in order to demonstrate the advantages of the annealed distal portion.

Conventional cannulas, like cannula 60, have very small outer diameters and walls that are very thin in order to fit into a root canal. However, when conventional cannulas, attempt to negotiate a curved portion of a root canal, difficulties can be encountered. As discussed above, the distal insertion end may cause the formation of a ledge in the root canal sidewall particularly the concave side of a curved portion in the root canal. Once a ledge is formed, it becomes difficult to advance an instrument beyond the ledge and it may also create the mistaken impression that the apex has been reached. The most extreme curvatures that are typically encountered usually occur within the last several millimeters of the root canal just above the apex. Accordingly, it is highly advantageous to have only the distal portion of the cannula annealed as it encounters a higher degree of curvature than the remainder of the cannula. For example, note the manner in which distal portion 65' flexes as shown in FIG. 3B and then enables the remainder of the cannula to be guided in a similar curved fashion downward toward apex 96 of root canal 92 as shown in FIG. 3C. In addition to minimizing the possibility of ledging, the present invention also diminishes the likelihood that the cannula will bend in a manner that prevents the delivery of the irrigant from the cannula as result of a curving when encountering a curvature in the root canal.

While the cannulas of the present invention may be formed from any suitable metal or alloy, they are preferably formed from stainless steel. The stainless steel is preferably an alloy that belongs to the class known as conventional austenitics or conventional austenitic stainless steel. A conventional austenitic stainless steel that is preferred for manufacturing embodiments of this invention is stainless steel 304. Other conventional austenitic stainless steels include types 301, 302, 303, 305, 308, 309, 310, 316, and 317. The preferred flexibility is conferred to the tips of cannulas manufactured according to this invention by annealing such tips while keeping the remainder or proximal portions of the cannulas untreated.

Annealing is a form of heat treatment applied to a metal to soften it, relieve internal stresses and instabilities, and make it easier to work or machine. It consists of heating the metal to a specified temperature for a specified time, both of which depend on the metal involved, and then allowing it to cool slowly. Annealing temperatures for conventional austenitic steels are at least 1000° C. (1800° F.). Embodiments of this invention comprise tips that distal portion that have been annealed by heating them to temperatures in the range 1600° F.–1800° F. This process is preferably performed in an oxygen free environment, such as a nitrogen or helium atmosphere, in order to avoid discoloration. In addition to the use of inert gases, the annealing is preferably achieved through the use of induction heating. More particularly, the heat is preferably generated by copper coils or tubing that receives alternating current in order to create a magnetic field. The cannula is held within the coils or tubing so that the portion to be annealed is surrounded. The magnetic field excites the electrons in the metal cannula which generates heat.

Although, heat transfers through the metal, the portion of the cannula that is not directly adjacent the coils does not reach the recystallization temperature or annealing temperature. Accordingly, an advantage of annealing through the use of a magnetic field is that the heat is transferred in a very localized manner. For example, when annealing a portion of the cannula in such a manner, the transition zone between the annealed portion and the nonannealed portion is typically only 1.5 mm in length. Stated otherwise, the portion directly opposite from or parallel to the coils is annealed and 1.5 mm beyond the end of the coil the cannula is not annealed.

Annealing the tips of cannulas according to the present invention in the presence of oxygen leads to discolored tips. However, this is not necessarily an entirely undesirable feature because discoloration can be regarded as indicative that a particular cannula has an annealed portion. Since the introduction of small amounts of metal oxides such as nickel oxide, chromium oxide or iron oxide in a root canal is not viewed as a concern under current endodontic practice, discolored distal portion may be useful. Accordingly, the annealed portion of the cannula may be formed by merely holding the portion in proximity to an open flame.

The length of the annealed portion relative to the length of the cannula that extends from the hub may vary depending on the percentage of the cannula that has been annealed. Note that since the endodontic irrigator tips have cannulas with different lengths, the length of the annealed portion also varies depending on the length of the cannula. Accordingly, the annealed portions are described below as a percentage of the cannula length and also specific lengths are provided for the annealed portions.

Since almost all of the cannula that extends from the hub may be annealed or only a very small segment may be annealed, the ratio of the annealed portion to the length of the cannula that extends from the hub may range from only 0.5% to about 90% and more precisely, may range from about 10% to about 85%. However, when only a very small segment is annealed then there may be insufficient flexibility for some uses. In contrast, if too much of the cannula is annealed then it may be difficult to control the movement. While an endodontic irrigator tip may have a cannula with an annealed distal portion that provides a ratio in the ranges provided above, the unannealed proximal portion is preferably long enough and rigid enough to enable it to force the annealed portion downward even as curvatures in the root canal are encountered. Further, the length ratios are preferably optimized such that the combination of a flexible annealed distal portion with a rigid proximal portion yields the optimal combination of control and flexibility. To ideally achieve these objectives, the ratio is preferably in a range from about 15% to about 75%, is more preferably in a range from about 20% to about 60%, and is most preferably no greater than about 50% such as the range from about 20% to about 35%.

As indicated above, the length of the annealed portion may vary depending on the length of the cannula, which may range from about 10 mm to about 35 mm. Use of the broadest ratio of 0.5% to 90% in combination with cannula lengths ranging from about 10 mm to about 35 mm yields a range of annealed portions lengths of 0.5 mm to about 31.5 mm. While the extremes of such a range have certain uses, the length of the annealed portion is in a narrower range to optimally achieve the combination of a flexible annealed distal portion with a rigid proximal portion that provides sufficient control and flexibility to be directed downward and to negotiate the curvatures that are encountered. For the most typical cannula lengths such as a cannula that has a length that is 25 mm, 21 mm, 17 mm, etc., the annealed portion preferably has a length that is in a range from about 2 mm to about 12 mm, more preferably about 3 mm to about 10 mm, and most preferably in a range from about 5 mm to about 8 mm. Cannula 60 of irrigator tip 20 in FIG. 1A is an example of a cannula extending from a hub that has a length that is about 21 mm with an annealed distal portion that is 7 mm in length. Cannula 60' of irrigator tip 20' in FIGS. 2A–2B and FIGS. 3B–3C is an example of a cannula extending from a hub that has a length that is 7.5 mm with an annealed distal portion that is 25 mm in length. Cannulas such as cannula 60 or cannula 60' provide ideal configurations for achieving the objectives discussed above. Note that the unannealed proximal portion is flexible enough to follow the annealed portion after the annealed portion has curved within the root canal as shown in FIGS. 3B–3C.

While the endodontic irrigator tip may have many suitable configurations, irrigator tip 20 and tip 20' are described in detail in order to provide disclosure of preferred configurations. Irrigator tip 20' has a hub that is configured similarly to the hub of the irrigator tip discussed in U.S. Pat. No. 6,079,979 entitled Endodontic Irrigator Tips and Kits which issued to Francesco Riitano and is owned by Ultradent Products Inc. U.S. Pat. No. 6,079,979 is hereby incorporated by reference.

Note that the same numerals are used to identify the corresponding elements of each embodiment with prime symbols being used to indicate the element in reference to a specific embodiment. So it should be understood that reference to an element and its corresponding number as shown in the drawings is also descriptive of the same element in other embodiments unless indicated otherwise by particular reference to the element. Reference is made primarily to the configuration of tip 20 and its elements are discussed and contrasted with the corresponding elements of the other embodiments, primarily tip 20'. Note that the features of the elements disclosed herein may be combined in any suitable fashion so, for example, cannula 60 may have a rounded rim defining its outlet orifice like rounded rim 66' instead of squared rim 66.

The hub is preferably designed to be coupled to means for dispensing fluid to the tip. Examples of the means for dispensing fluid to the tip include a syringe, a ratcheting device which increases in pressure upon ratcheting to deliver liquid, or a threaded plunger. Hub 22 further includes a male or female Luer lock component 23, or a standard thread which mates with another thread to engage the syringe or similar device. Such lock components and standard threads are examples of means for coupling the proximal end of the hub to the fluid dispensing means. The hub preferably has a feature that provides a grasping surface for positioning the tip on a syringe. Hub 22 has wings 27 extending longitudinally from body 24 while hub 22' has ridges 27' extending longitudinally from body 24" and neck 40". The hub may also be an integral extension of a device such as a syringe. Of course a hub that is integral with a syringe does not need grasping surfaces such as wings 27 or ridges 27'.

Hub 22 has two primary components including body 24 and neck 40. Body 24 and neck 40 are depicted in FIG. 1A as integral components and accordingly body 24 and neck 40 are essentially portions of hub 22. Hub 22' also has an integral body 24' and neck 40'. Neck 40 is straight while neck 40' is the portion of hub 22' that is angled. The neck is preferably narrower than body 24, as depicted, in both embodiments. Although the body and the neck are depicted as integral portions of the hub, each may also be separate components. Accordingly, the body and the neck are discussed herein with reference to their respective proximal and distal ends.

Each body 24 has a proximal end 26 opposite from a distal end 28, the proximal end being the proximal end of the hub. Body 24 may also include a shoulder 30, which is a tapered portion of body 24, as shown by the embodiment depicted in FIG. 1A at 30. Although shoulder 30 is not necessary, it is preferred as it provides a gradual transition to neck 40. Note that the longitudinal axis of body 26' is identified at 32' to provide reference to the angled orientation.

Neck 40 of hub 22 has a proximal end 42 coupled to distal end 28 of body 24. Each neck has a distal end 44 opposite proximal end 42 which is the distal end of the hub. Note that the proximal end of hub 22 is proximal end 26 of body 24 and distal end of hub 22 is distal end 44 of neck 40. In one embodiment, the length of the neck 40 or 40' is in the range of about 3 to about 20 millimeters, more preferably about 4 to about 15 millimeters, and most preferably about 5 to about 12 millimeters.

A round nib 45 extends from distal end 44 around proximal end 62 of cannula 60 which is an exposed portion of a plug used to assist in retaining cannula 60 and in providing a seal around cannula 60. The plug is an adhesive that has been cured after the cannula has been positioned within neck 40. Any suitable adhesive may be utilized such as commercially available epoxies intended for gluing stainless steel to plastics such as polypropylene. Note that in contrast to the configuration of distal end 44, the distal end of neck 40' is a distal stop end 44' with a flat distal face 46'. The advantages of flat distal face 46' are discussed below in greater detail.

A cross-sectional view of hub 22 is not provided so the interior configuration of the hub is described in reference to hub 22' and the cross-sectional view thereof shown in FIG. 2B, however, hub 22 has a similar configuration and similar elements. Hub 22' has an interior surface 50' within body 24' and neck 40' that defines a hollow chamber 52'. Hollow chamber 52' has an inlet 54' that is an opening into hollow chamber 52' for fluid communication with the means for dispensing fluid to the tip. Hollow chamber 52' is an example of a chamber means for containing fluid within the hub as received from the means for dispensing fluid to the endodontic irrigator tip.

Cannula 60 has a proximal end 62 opposite a distal insertion end 64. A portion of proximal end 62 is sheathed within distal end 44 of neck 40 such that a portion of cannula 60 extends from distal end 44 of neck 40 with sufficient length to extend into a root canal of a tooth. Cannula 60 has an outer diameter which permits insertion of cannula 60 into a root canal of a tooth. Of course, it is preferable for cannula 60 to be generally flexible for advancement within a root canal.

Cannula 60 has an interior surface 70 defining a conduit 72. As best view and described in relationship to FIG. 2B, fluid enters conduit 72' from hollow chamber 52' via an inlet 74' located at proximal end 62' such that conduit 72' and hollow chamber 52' are in fluid communication. Fluid exits conduit 72' via outlet orifice 76' at distal insertion end 64', as best viewed in FIG. 2C or in FIG. 1B for tip 20. All of the cannulas disclosed herein are examples of delivery means for delivering fluid from the chamber means to a root canal of a tooth while inserted within the root canal.

Cannula 60 can be coupled to neck 40 in a fluid tight manner through a variety of means. In one embodiment, cannula 60 comprises a metal material while hub 22 is comprised of polycarbonate or another rigid material. In another embodiment, cannula 60 extends integrally from hub 22. The gauge of cannula 60 may be, for example, in the range of about 33 to about 18 gauge, more preferably about 31 to about 25 gauge, and most preferably, about 31 to about 27 gauge.

Cannula 60 is substantially straight and has a portion sheathed within distal end 44. An advantage of the configuration of tip 20' as shown best in FIG. 2B, is that cannula 60' is angled with respect to the longitudinal axis 32' of body 24' while distal stop end 44' is perpendicular with respect to cannula 60'. Due to the angled configuration, as shown in FIG. 3A, a practitioner is readily able to place cannula 60' of angled tip 20' into a root canal of a patient's tooth 90 while holding a syringe 100 coupled to tip 20' at an angle with respect to the patient's mouth. This angled configuration enables the practitioner to more easily insert the tip into a root canal and to move the tip within the root canal.

Distal stop end 44' is angled with respect to longitudinal axis 32' at any suitable angle. By way of example, in one embodiment the angle α is in the range of about 45° to about 180°, more preferably, about 60° to about 160°, most preferably, about 90° to about 140°. In the embodiment shown in FIGS. 2A–2B, the angle α is about 120°. The angle preferably enables a practitioner to maneuver the tip without concern for the position of structures other than the tooth being treated. For example, as shown in FIG. 3A, tip 20' can be moved while treating tooth 90 without any contact with the teeth on the opposite jaw by the practitioner's hand, syringe 100 or tip 20'.

Distal stop end 44' of neck 4' has a diameter that is substantially greater than the outer diameter of cannula 60'. Thus, as shown in FIGS. 3A–3C, distal stop end 44' acts as an integral stop to prevent penetration into the root canal 92 of endodontic irrigator tip 20' beyond the length of the portion of cannula 60' extending from distal stop end 44' of neck 40'. As shown, the practitioner is able to strategically, conveniently position distal stop end 44' on the rim of the occlusal surface of a crown and orient cannula 60' in a controlled manner within root canal 82'.

As shown, flat distal face 46' of distal stop end 44' is substantially perpendicular to cannula 60'. Since face 46' is oriented substantially perpendicular to cannula 60', face 46' can be reliably positioned in a secure manner on the crown of a tooth. As discussed above, FIG. 3B depicts cannula 60' inserted into root canal 92 past pulp chamber 94 with its distal annealed portion 65 curving as it encounters a curvature in root canal 92. Once distal annealed portion 65 has curved due to the curvature of the tooth or after encountering an outcropping then the remainder of cannula 60' follows and the cannula can be pushed downward until distal face 46' of distal stop end 44' engages crown 98 of tooth 90. Flat distal face 46' of distal stop end 44' prevents apical perforation since only the portion of cannula 60' extending from the stop can be inserted into root canal 92.

The appropriate working length of the cannula is determined by viewing radiographic images of the tooth. As shown in the Table 1 below, root canal lengths vary significantly based on the type of tooth. The lengths listed in Table 1 are average root canal lengths enountered for a particular type of tooth.

TABLE 1

| Average Root Canal Lengths | | |
| --- | --- | --- |
| Tooth | Upper | Lower |
| Central | 23 mm | 20.5 mm |
| Lateral | 22 mm | 21 mm |
| Canine | 26.5 mm | 25.5 mm |
| First Premolar | 20.5 mm | 20.5 mm |
| Second Premolar | 21.5 mm | 22 mm |
| First Molar | 20.5 mm | 21 mm |
| Second Molar | 20 mm | 20 mm |

Since various lengths are encountered, endodontic irrigator tips are preferably supplied in a kit with tips that have various cannula lengths. Such a kit can be used for root canals of all different lengths. Thus, in one kit for example, tips 20 are featured having working cannula lengths (i.e., the portion of cannula 60 extending past distal end 44 of neck 40 ) of about 17 mm, about 21 mm and about 25 mm. Note that the cannula preferably does not extend all the way to the apex of the root canal.

Of course, the cannulas may have a broader range of working lengths depending on the manner in which the cannula is inserted into the root canal. For example, cannula 60 may have a working length ranging from about 10 to about 35 millimeters, from about 12 to about 30 millimeters, or from about 14 to about 28 millimeters. Additionally, the kit may include a large number of tips wherein the length of each cannula increases incrementally, for example, about 0.5 mm to about 1 mm, between each subsequent tip in the kit, such that the kit includes working cannula lengths about 17, about 17.5 mm, about 18 mm, and so on up to about 25 mm in increments of one-half a millimeter.

Because the kit features different cannula working lengths, the practitioner can choose the working length of a cannula needed for any root canal procedure, fine tuning the working length of each tip, such that the cannula selected delivers fluid to the precisely desired location. The kit can thus be used in root canals having a variety of different lengths.

FIG. 1B is an enlarged, cross-sectional view of the distal insertion end 64 of cannula 60 shown in FIG. 1A. Note that FIG. 2C depicts an enlarged, cross-sectional view of the distal insertion end 64' of cannula 60' shown in FIGS. 2A–2B. In the embodiment depicted in FIG. 1B, distal insertion end 64 has a rounded rim 66 which defines outlet orifice 76 in contrast to the conventional squared rim 66' of distal insertion end 64' shown in FIG. 2C. While a squared rim may be utilized, the rim is preferably round. The curved or bull nose configuration of rounded rim 66 is highly advantageous when moving cannula in an up and down fashion. As discussed above, ledges can occur when a practitioner attempts to insert the distal insertion end of an irrigator tip as far as the apex of the root canal and the distal insertion end is halted prematurely against the sidewall of the root canal. The downward pressure exerted on the distal insertion end can cause the distal insertion end to dig into the side of the root canal and form a ledge. Such ledges are difficult to bypass; and if the ledge occurs very close to the apex, the ledge may give the practitioner the mistaken impression that the apex has been reached. The curved configuration of rounded rim 66 provides less frictional contact than does squared rim 66' and therefore minimizes the potential for causing ledging. So when resistance is encountered, it is easier for the distal insertion end 64 with rounded rim 66 to slide off or around the structure in the root canal that has blocked its path and to then progress further down into the root canal.

Rounded rim 66 may be formed by any suitable methodology. One method involves mounting hub 22 on a rotating spindle and then spinning the rim against a curved abrasive structure configured to round off the squared edge.

Like a cannula with an annealed distal portion that terminates at a rounded rim, a cannula that it is not annealed along any portion of its length may also terminate at a rounded rim. For example, cannula 60 may also be an unannealed cannula that terminates at a rounded rim. A rounded rim is especially useful with an unannealed cannula since the unannealed cannula is less capable of flexing within the root canal when compared with a cannula that has an annealed distal portion. So, as discussed above with regard to cannulas that have an annealed distal portion, when an unannealed cannula reaches a curvature within the root canal and resistance is encountered, a rounded rim assists in enabling the cannula to be further advanced downward by sliding against the root canal surfaces.

Hub 22' is preferably being rigid so that neck 40' retains its angled configuration. However, neck 40' may be either rigid and straight or flexible. It may be flexible so that it can be selectively bent to a desired location by the practitioner, yet be sufficiently rigid to remain in the desired location until bent again by the practitioner. Accordingly, neck 40' may be formed from a rigid plastic which can become bendable upon heating and then rigid again after subsequent cooling.

FIGS. 4A–4C depict a plurality of cannulas 160a–c having various distal insertion ends 164a–c and various outlet orifices 176a–c. Cannula 160 a has a pointed distal insertion end 164a adapted for aggressive movement within the root canal while cannula 160b has a rounded distal insertion end, Note that both distal insertion end 164a and 164b are closed so that the outlet orifices 176a and 176b are in the sidewalls of their respective cannulas. This sideported configuration is useful in some circumstances, particularly when working very close to the apex as it buffers the impact of the flow of the liquid, thereby minimizing the likelihood of apical perforation. FIG. 4C depicts another embodiment wherein the outlet orifice is a slot 176c extending from the distal insertion end upward and tapering into the sidewall of cannula 160c such that a portion of conduit 172c is exposed.

The last several millimeters of the cannula may also be annealed to provide for greater flexibility at the distal portion of the cannula. Additional details regarding annealed cannulas arc provided in U.S. patent application Ser. No. 09/766,708 entitled Endodontic Irrigator Tips Having Fiber Covered Cannulas and Related Methods which was filed on Jan. 22, 2001. Ser. No. 09/766,708 is hereby incorporated by reference, The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. An endodontic irrigator tip comprising:
   a hub comprising proximal and distal ends and a hollow interior chamber through which fluid is delivered;
   a single, integrated tip means, attached to the distal end of said hub, for delivering fluid to a root canal of a tooth, and comprising,
      first means at a distal portion of the tip means, for providing an annealed, flexible portion which is bendable and conformable to the root canal as the tip means traverses the root canal; and
      second means at a proximal portion of the tip means, for providing a non-annealed, more rigid portion which facilitates traversing the root canal with said tip means.

2. An endodontic irrigator tip as recited in claim 1, wherein the tip means comprises a conduit defined by an interior surface of the delivery means, the conduit receiving fluids via the hollow interior chamber of the hub and said conduit terminating at an outlet orifice such that fluids can be delivered through the conduit and out of the outlet orifice.

3. An endodontic irrigator tip as recited in claim 2, wherein the outlet orifice is defined by a rounded rim.

4. An endodontic irrigator tip as recited in claim 1, further comprising means for coupling the proximal end of the hub to a source for dispensing fluid to the irrigator tip.

5. An endodontic irrigator tip as recited in claim 1, wherein the tip means has a length in a range from about 10 millimeters to about 35 millimeters.

6. An endodontic irrigator tip as recited in claim 1, wherein the tip means has a conduit with a gauge in a range from about 33 gauge to about 18 gauge.

7. An endodontic irrigator tip as recited in claim 1, wherein the tip means has a length such that there is a ratio between the length of the annealed portion and the overall length of the tip means ranging from about 0.5% to about 90%.

8. An endodontic irrigator tip as recited in claim 1, wherein the tip means has a length such that there is a ratio between the length of the annealed portion and the overall length of the tip means ranging from about 20% to about 60%.

9. An endodontic irrigator tip as recited in claim 1, wherein the tip means has a length such that there is a ratio between the overall length of the annealed portion and the length of the tip means ranging from about 20% to about 35%.

10. An endodontic irrigator tip as recited in claim 1, wherein the annealed portion has a length in a range from about 0.5 mm to about 31.5 mm.

11. An endodontic irrigator tip as recited in claim 1, wherein the annealed portion has a length in a range from about 2 mm to about 12 mm.

12. An endodontic irrigator tip as recited in claim 1, wherein the annealed portion has a length in a range from about 5 mm to about 8 mm.

13. An endodontic irrigator tip comprising:
a hub comprising proximal and distal ends, and a hollow chamber defined by an interior surface of the hub, wherein the hollow chamber has an inlet for providing fluid communication with a source of fluid;
a one-piece cannula extending from the distal end of the hub with a length and outer diameter that permits insertion of the cannula into a root canal of a tooth, the cannula comprising,
a conduit defined by an interior surface of the cannula,
an inlet that is in fluid communication with the hollow chamber of the hub,
an outlet orifice located at the distal insertion end of the cannula such that fluids can be delivered from the hollow chamber, through the conduit and then out of the outlet orifice,
an annealed distal portion which is bendable and conformable to the root canal as the tip means traverses the root canal, and
a non-annealed, more rigid portion which facilitates traversing the root canal with said cannula.

14. An endodontic irrigator tip as recited in claim 13, further comprising means for coupling the proximal end of the hub to the source of fluid.

15. An endodontic irrigator tip as recited in claim 13, wherein the cannula has a length in a range from about 10 millimeters to about 35 millimeters.

16. An endodontic irrigator tip as recited in claim 13, wherein the cannula has a conduit with a gauge in a range from about 33 gauge to about 18 gauge.

17. An endodontic irrigator tip as recited in claim 13, wherein the cannula has a length such that there is a ratio between the length of the annealed portion and the length of the cannula ranging from about 0.5% to about 90%.

18. An endodontic irrigator tip as recited in claim 13, wherein the cannula has a length such that there is a ratio between the length of the annealed portion and the length of the cannula ranging from about 20% to about 60%.

19. An endodontic irrigator tip as recited in claim 13, wherein the cannula has a length such that there is a ratio between the length of the annealed portion and the length of the cannula ranging from about 20% to about 35%.

20. An endodontic irrigator tip as recited in claim 13, wherein the annealed portion has a length in a range from about 0.5 mm to about 31.5 mm.

21. An endodontic irrigator tip as recited in claim 13, wherein the annealed portion has a length in a range from about 2 mm to about 12 mm.

22. An endodontic irrigator tip as recited in claim 13, wherein the annealed portion has a length in a range from about 5 mm to about 8 mm.

23. An endodontic irrigator tip as recited in claim 13, wherein the outlet orifice is defined by a round rim.

* * * * *

UNITED STATES PATENT AND TRADEMARK OFFICE
CERTIFICATE OF CORRECTION

PATENT NO. : 6,422,865 B1
DATED : July 23, 2002
INVENTOR(S) : Dan E. Fischer

It is certified that error appears in the above-identified patent and that said Letters Patent is hereby corrected as shown below:

Column 1,
Line 40, after "Products," replace "Inc" with -- Inc. --

Column 2,
Line 7, after "invention" insert -- is --
Line 62, after "of" replace "a" with -- an --

Column 3,
Line 12, at the beginning of the line, delete "FIGS." and replace with -- FIG. --
Line 15, after "4A" delete "provide"
Line 28, after "to" replace "delivery of" with -- deliver --
Line 29, after "as" replace "debreeding" with -- debriding --

Column 4,
Line 38, after "tips that" delete "distal portion that"
Line 53, after "the" replace "recystallization" with -- recrystallization --

Column 7,
Line 39, after "best" replace "view" with -- viewed --

Column 9,
Line 30, after "cannula" insert -- 60 --

Signed and Sealed this

Eighteenth Day of March, 2003

JAMES E. ROGAN
*Director of the United States Patent and Trademark Office*